US006161040A

United States Patent [19]

Blunsden

[11] Patent Number: 6,161,040

[45] Date of Patent: Dec. 12, 2000

[54] CURRENT LIMITER FOR AN IMPLANTABLE CARDIAC DEVICE

[75] Inventor: Christopher K. Blunsden, West Pymble, Australia

[73] Assignee: Pacesetter, Inc., Sylmar, Calif.

[21] Appl. No.: 09/250,357

[22] Filed: Feb. 16, 1999

[51] Int. Cl.[7] ........................ A61N 1/39

[52] U.S. Cl. ........................ 607/5

[58] Field of Search ........................ 607/5

[56] References Cited

U.S. PATENT DOCUMENTS

| | | | |
|---|---|---|---|
| 3,653,387 | 4/1972 | Ceier | 607/5 |
| 4,164,215 | 8/1979 | Finlayson et al. | 607/5 |
| 4,637,397 | 1/1987 | Jones et al. | 607/5 |
| 4,745,923 | 5/1988 | Winstrom . | |
| 5,433,732 | 7/1995 | Hirschberg et al. . | |
| 5,591,218 | 1/1997 | Jacobson | 128/908 |

*Primary Examiner*—William E. Kamm
*Attorney, Agent, or Firm*—Gottlieb Rackman & Reisman PC

[57] ABSTRACT

A defibrillator for applying bipolar or multipolar shock pulses includes an energy source, a sensor circuit for sensory intrinsic cardiac activity, a controller for applying pulses from said energy source and a protection circuit. The protection current monitors the current to the sensory circuit and limits the same to a predetermined level. The current is monitored during different phases of the pulses by appropriate limiter sections. Preferably the limiter sections are active semiconductor device which are energized all the time.

13 Claims, 2 Drawing Sheets

CURRENT LIMITER FOR AN IMPLANTABLE CARDIAC DEVICE

BACKGROUND OF THE INVENTION

1. Field of Invention

This invention pertains to an implantable cardiac device such as a defibrillator wherein a high voltage pulses are applied to a patient to provide antitachycardia therapy. More particularly, the present invention pertains to an ICD having an automatic current limiting circuit.

2. Description of the Prior Art

Patients suffering from tachycardia (a higher than normal heart rhythm) are frequently treated with a defibrillator which is adapted to provide appropriate therapy. Typically this therapy consists of high voltage (relatively high energy content, shocks applied to the cardiac tissues. Frequently, the defibrillator is provided as an implantable cardiac device (ICD) installed surgically into the patient, typically at a site remote from the heart itself. Electrodes are also provided which have tips secured to externally to the heart, or internally for endo leads with leads connecting the electrodes to the defibrillator. The energy for the defibrillation shocks derived by the defibrillator is provided by one or more capacitors which, prior therapy, are charged to a nominal voltage and then discharged during shocks.

A problem with defibrillators is that because the impedance of the heart tissues through which the shocks are discharged is unknown and hence, it is difficult to control the current delivered during the shocks. Abnormally high current levels are undesirable because a high current may damage the heart tissues. It has been proposed, for example in U.S. Pat. Nos. 5,433,732 and 4,745,923 that current limiters be provided in series with one of the electrodes to thereby limit the maximum current that is delivered to the heart tissues during antitachycardia therapy. However, this approach is effective only if shocks of a single phase are applied. The approach is not effective for multi-polar-phase shocks. Moreover, the circuitry provided for the limiters is fairly complicated and uses a large number of components.

OBJECTIVES AND ADVANTAGES OF THE INVENTION

An objective of the present invention is to provide an implantable defibrillator with a means of effectively protecting its sensing circuit from overvoltage during defibrillation shocks.

A further objective is to provide an effective protection circuit for a defibrillator which can protect a sensing circuit thereof during multiphasic defibrillation pulses.

A further objective is to provide a protection circuit which can be easily and effectively implemented without changing drastically the design of the defibrillators.

Other objectives and advantages of the invention shall become apparent from the following description. Briefly, a defibrillator constructed in accordance with this invention includes a power supply, which is typically a battery, a charger for charging from the battery a capacitor to a predetermined voltage and a switching bridge arranged to selectively discharge the capacitor through a pair of defibrillator electrodes into the heart to generate multi-phasic shocks.

The defibrillator further includes a sense/pacing circuit which senses the intrinsic activity of the heart and can selectively generate pacing pulses through corresponding sense/pacing electrodes, and a controller which controls the defibrillation and pacing processes.

Advantageously, the defibrillator is also provided with a protecting circuit for protecting the sense/pacing circuit from overvoltage due to defibrillation shocks. The protection circuit includes separate current limiting sections for sensing current during positive and negative defibrillation shocks, each section limiting these currents to predetermined threshold. A biasing circuit is used to bias each of the current limiting- sections. Advantageously for multi-chamber devices, similar protection circuits may be provided, all sharing a common biasing circuit.

DETAILED DESCRIPTION OF THE INVENTION

Figure 1:
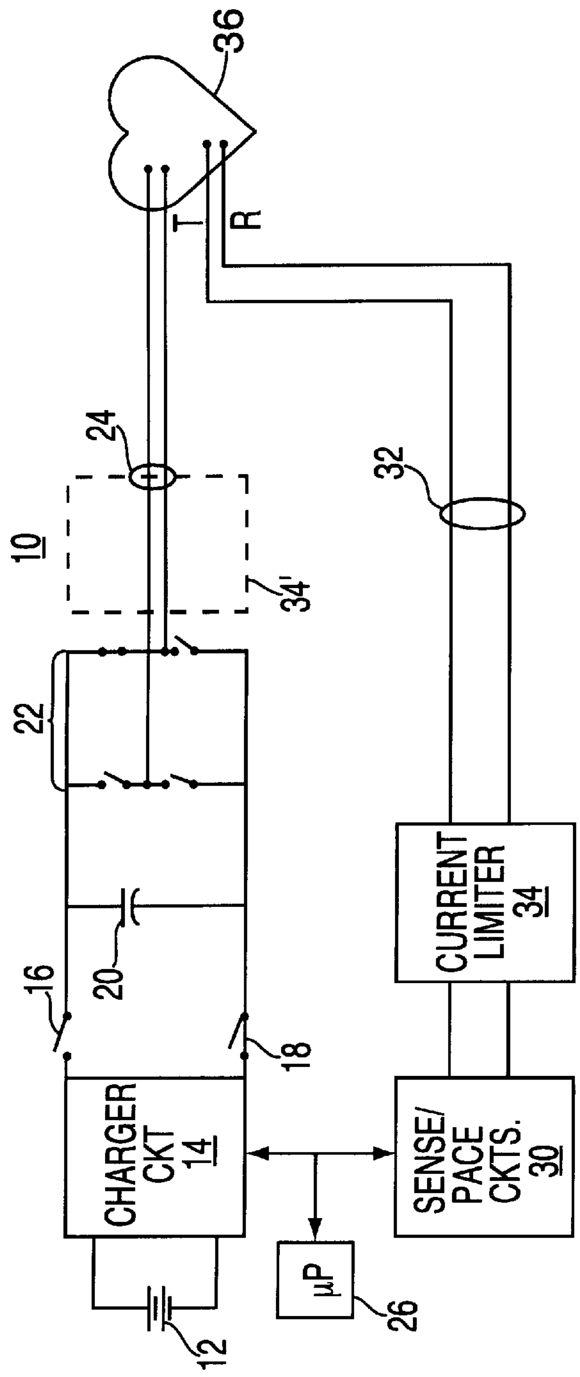
FIG. 1 shows a block diagram of an ICD constructed in accordance with this invention.

Referring first to FIG. 1, a defibrillator 10 constructed in accordance with this invention consists of a battery 12, a charging circuit 14, switches 16, 18, a capacitor 20, a switching bridge 22 and charge delivery electrodes 24. The defibrillator (or ICD) 10 further includes a controller or microprocessor 26. The ICD 10 further includes a sense/pace circuits 30 which sense the intrinsic activities in the patient's heart 36 through a tip and a ring electrode collectively identified as 32.

Controller 26 monitors the heart 36 through electrodes 32 or by other means and, if necessary, generates commands either to sensory/pace circuits 30 to generate antibradicardia therapy or to charger 14 and switches 16, 18, 22 to apply cardiovascular therapy or defibrillation shocks in a known manner.

Importantly, a protection circuit such as a current limiter 34 is also provided to protect the sense/pace circuit 30, from overvoltage during defibrillation shocks as described more fully below. In FIG. 1 a single sense/pace circuit 30 is shown with an associated protection circuit 34, it being understood that this circuit 30 may be used to sense/pace after the atrium or ventricle of the heart 36. Alternatively, two circuits 30 and two sense/pace protection circuits 34 may be provided, one for each of the cardiac chambers.

Figure 2:
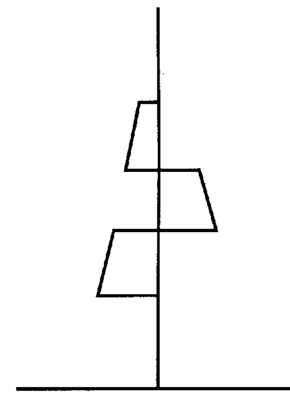
FIG. 2 shows a multipolar shock used for defibrillation.

Typically, the controller 26 senses the cardiac condition of the patient, and when fibrillations are detected, generates commands for a series of defibrillation shocks. The shocks can be unipolar, or, as shown in FIG. 2, they could have two or more shock components of alternate polarities. These defibrillation shock pulses are generated as follows.

First, the controller 26 closes switches 16 and 18 causing the charger circuit 14 to charge capacitor 20 to a predetermined voltage using energy from battery 12. When the capacitor is charged, switches 16, 18 are opened and the switches of bridge 22 are closed in a predetermined sequence to provide a composite shock pulse to the heart 36 through electrodes 24.

Figure 3:
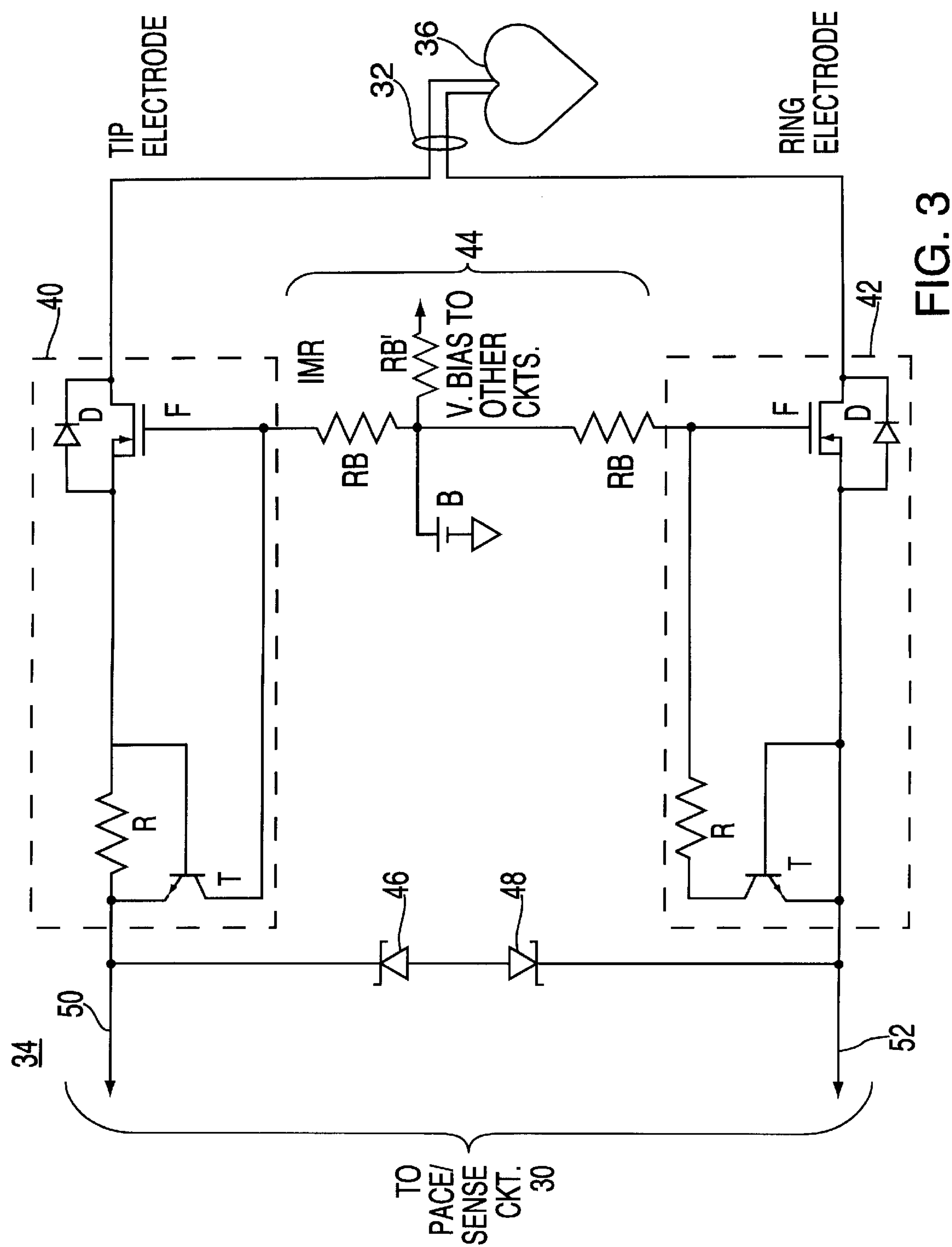
FIG. 3 shows details of the current limiting circuitry for the ICD of FIG. 1.

Details of the protection circuit 34 are shown in FIG. 3. This circuit 34 consists of a pair of limiting circuits 40, 42 and a common biasing circuit 44, as well as a pair of Zener diodes 46, 48 used to clip the maximum voltage across the input lines 50, 52. Each of the limiting circuits includes a resistor R, a transistor T, and an FET F. Preferably transistors T are BJT NPN transistors rated at a maximum of about 20 volts. The FETs F are preferably n-channel mosfet devices rated at 1000 volts and have a parasitic diode D.

The biasing circuit 44 includes a battery B and biasing resistors RB, one resistor RB for each limiting circuit.

The circuitry shown operates as follows. The biasing circuit 44 is arranged to maintain the FETs F in an energized or closed state at all times. When the appropriate switches of bridge 22 are closed a positive voltage is applied between input lines 50, 52 causing current to flow through resistor R of and the FET F circuit 40 to the tip electrode, through heart 36 and then back through ring electrode, circuit 42 and input line 52. The resistor R of circuit 40 is selected to monitor and limit this current to a preselected limit. More specifically the circuit to sense and stimulate a second cardiac chamber 40 limits the current I to the value:

$$Io=0.6/R$$

If the current exceeds this value, the voltage across resistor R turns the transistor T on. When transistor T is on, it causes the voltage of the gate of FET F to be clamped thereby preventing any further increase in the current beyond Io. Once the current reaches a predetermined threshold level for example 100 milliamps, the transistor T turns on shifting the bias on the FET F to limit the current to this value.

As previously mentioned, preferably each stimulation pulse is composed of several components of alternate phases. The above operation is effective for all the positive phases.

For the negative phase(s) the limiter circuit 42 performs the limiting operation in an identical manner.

Moreover the invention disclosed herein can be easily extended to multi-electrode stimulation schemes. For example if other electrodes are used to sense and stimulate a second cardiac chamber, then electrodes may be provided with a protective circuit which shares the same biasing circuit through a resistor RB'.

In summary, the subject invention provides advantageous current limiting using a circuitry which requires less number of components then the prior art. In addition, the circuitry introduces less loop resistance then other prior art circuits. This feature is particularly important because, first, a lower resistance reduces the attenuation of the stimulation pulses. Therefore the stimulation pulses are more effective.

Prior art limiters required an additional power cell as a source for the current limiting circuitry. In the present invention, the biasing circuit can be powered from the same source as the defibrillator.

Finally, because the main FET's are always activated, the protective circuit is capable of operating much faster and therefore can react for example to inrush current since it does not need time to power up.

Finally, while the protective circuit 34 is shown as protecting the pace/sense circuit 30 from overvoltage due to defibrillator shock, a similar circuit may also be provided between switch bridges 22 and electrodes 24 to protect heart 36 from high current levels.

Although the invention was described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. A defibrillator for implantation into a patient to provide therapy to a patient's heart, comprising:

a pulse generator generating selectively defibrilliation pulses, said defibrilliation pulses having positive and negative phases;

defibrillator electrodes for delivering said defibrilliation pulses to said heart;

first and sensing electrodes extending to said heart;

a sensing circuit sensing intrinsic activity within said heart; and a protection circuit arranged between sensing electrodes and said sensing circuit to protect said sensing circuit from an overvoltage resulting from said defibrilliation pulses, said protection circuit including a first section and a second section;

wherein said first section and a second section each include an electronic element arranged to limit current during said positive phase and said negative, respectively; and a biasing circuit disposed in said protection circuit and shared by said first and second sections for biasing said electronic elements.

2. The defibrillator of claim 1 wherein said first section is in series with said first sensing electrode and wherein said second section is in series with said second sensing electrode.

3. The defibrillator of claim 1 wherein each of said active semiconductor elements include an FET having a source and a drain in series with one of said electrodes and a gate coupled to said biasing circuit.

4. The defibrillator of claim 3 wherein said biasing circuit is arranged to maintain said FETs on continuously.

5. The defibrillator of claim 3 wherein each said section further comprises a current sensor for sensing current through said FET and a limiting element coupled to said sensor that adjusts the bias of said FET to a preset threshold if said current as sensed by said sensor exceeds a preset limit.

6. The defibrillator of claim 5 wherein said sensor is a resistor in series with one of said drain and said source.

7. The defibrillator of claim 5 wherein said limiting element is a transistor.

8. An implantable defibrillator comprising:

a power source;

a capacitor;

a charger for selectively charging said capacitor;

a first and a second defibrillator electrode arranged to deliver bipolar stimulation pulses to the heart of a patient;

an electronic switch selectively coupling said capacitor to said electrodes;

a controller that operates said electronic switch to discharge said capacitor through said electrodes to generate bipolar defibrilliation pulses of predetermined shapes;

first and second sensing electrodes;

a sensor circuit coupled to said first and second sensing electrodes and arranged to sense an intrinsic activity of the heart; and a protection circuit between said heart and said protection circuit limiting the current to said protector corresponding to said bipolar defibrilliation pulses, said protection circuit including a first current limiting switch coupled to said first sensing electrode, a second current limiting switch coupled to said second sensing electrode and a biasing circuit shared by said first and second limiting switches and arranged to bias said first and second current limiting switches.

9. The defibrillator of claim 8 wherein said defibrilliation pulses include a positive and a negative component, and wherein said protection circuit includes a first section for limiting current corresponding to said positive component and a second section for limiting current corresponding to said negative component, said first section including said first current limiting switch and said second section including said second current limiting switch.

10. The defibrillator of claim 9 wherein said first section is coupled in series with said first sensing electrode and said second section is coupled in series with said second sensing electrode.

11. The defibrillator of claim 10 wherein each said current sensing element includes an active semiconductor element in series with one of said sensing electrodes, a current sensor for sensing current flowing through said current sensing element and a limiting element sensing said current and limiting said current if said current exceeds a predetermined threshold.

12. The device of claim 11 wherein said active semiconductor element is a MOSFET.

13. The device of claim 10 wherein said current limiting element is a BJT transistor.

* * * * *